United States Patent [19]

Champney, Jr.

[11] Patent Number: 5,599,584

[45] Date of Patent: Feb. 4, 1997

[54] MICROMINIATURE COMBUSTIBLE GAS SENSOR AND METHOD OF FABRICATING A MICROMINIATURE COMBUSTIBLE GAS SENSOR

[75] Inventor: Richard E. Champney, Jr., Beaver Falls, Pa.

[73] Assignee: Mine Safety Appliances Company, Pittsburgh, Pa.

[21] Appl. No.: 357,031

[22] Filed: Dec. 16, 1994

[51] Int. Cl.$^6$ ........................................... B01J 37/00
[52] U.S. Cl. ...................... 427/245; 427/259; 427/272; 427/282; 502/527
[58] Field of Search .................. 427/245, 259, 427/272, 282, 372.2; 502/527

[56] References Cited

U.S. PATENT DOCUMENTS

| | | |
|---|---|---|
| 3,092,799 | 6/1963 | Baker . |
| 4,045,177 | 8/1977 | McNally . |
| 4,072,467 | 2/1978 | Jones . |
| 4,313,907 | 2/1982 | McNally . |
| 4,315,956 | 2/1982 | McNally . |
| 4,332,772 | 6/1982 | McNally . |
| 4,355,056 | 10/1982 | Dalla et al. . |
| 5,250,170 | 10/1993 | Yagawara et al. . |
| 5,262,127 | 11/1993 | Wise et al. . |
| 5,282,948 | 2/1994 | Cole et al. . |
| 5,345,213 | 9/1994 | Semancik et al. . |

OTHER PUBLICATIONS

Krebs, P. and Grisel, A., "A Low Power Integrated Catalytic Gas Sensor," *Sensors and Actuators* B, 13–14, 155–58 (1993).

Wu, Q. et al., "Development of Chemical Sensors Using . . . ", *Sensors and Actuators* B, 13–14, 1–6 (1993).

Goldberg, H. D. et al., "Screen Printing: A Technology for the Batch Fabrication . . . ", *Sensors and Actuators* B, 21, 171–83 (1994).

Pollak–Diener, G. and Obermeier, E., "Heat–Conduction Microsensor . . . " *Sensors and Actuators* B, 13–14, 345–47 (1993).

Wiegleb, G. and Heitbaum, J., "Semiconductor Gas Sensor . . . " *Sensors and Actuators* B, 17, 93–99 (1994).

Aigner, R. et al., "Sinusoidal Temperature Modulation of the Si–Planar Pellistor," *Sensors and Actuators* B, 18–19, 143–47 (1994).

Gall, M., "The Si Planar Pellistor . . . ", *Sensors and Actuators* B, 4, 533–38 (1992).

Accorsi, A. et al., "A New Microsensor for Environmental Measurements", *Sensors and Actuators* B, 4, 539–43 (1991).

Mosely, P. T. and Tofield, B. C., ed., *Solid State Gas Sensors*, Adams Hilger Press, Bristol, England, Chapter 2 (1987).

*Primary Examiner*—Asok Pal
*Attorney, Agent, or Firm*—James G. Uber; Henry E. Bartony, Jr.

[57] ABSTRACT

A microminiature combustible gas sensor and a method of fabricating a microminiature combustible gas sensor are provided in which the catalytically active detector comprises a high surface area refractory catalyst support. A microminiature combustible gas sensor is also provided which comprises a catalytically active detector and a diffusion/flow restrictor for limiting the amount of combustion fuel reaching the catalytically active detector. The restrictor causes the catalytic reaction occurring in the vicinity of the catalytically active detector element to become substantially diffusion limited and reduces the power requirements of the sensor. The restrictor also reduces convective heat losses which may arise because of the large temperature gradient surrounding the catalytically active detector element. Finally, a microminiature combustible gas sensor comprising a flashback arrestor with one or more generally linear capillaries for preventing flashback is provided.

10 Claims, 11 Drawing Sheets

MICROMINIATURE COMBUSTIBLE GAS SENSOR AND METHOD OF FABRICATING A MICROMINIATURE COMBUSTIBLE GAS SENSOR

FIELD OF THE INVENTION

The present invention relates to a combustible gas sensor and more particularly to a microminiature combustible gas sensor as well as to a method of fabricating a microminiature combustible gas sensor.

BACKGROUND OF THE INVENTION

Combustible (flammable) gas sensors have been in use for many years for the prevention of accidents caused by the explosion of combustible or flammable gases. In general, combustible gas sensors operate by catalytic oxidation of combustible gases. Conventional gas sensors typically comprise a platinum wire assembly encased in a refractory (for example, alumina) bead, which is impregnated with a catalyst. This encased assembly is commonly referred to as a pelement or a pellistor. A detailed discussion of pelements and catalytic combustible gas sensors which include such pelements is found in Mosely, P. T. and Tofield, B. C., ed., *Solid State Gas Sensors*, Adams Hilger Press, Bristol, England (1987).

In general, the pelement operates as a small calorimeter which measures the energy liberated upon oxidation of a combustible gas. The platinum element serves two purposes within the pelement: (1) heating the bead electrically to its operating temperature (typically approximately 500° C.) and (2) detecting the rate of oxidation of the combustible gas.

The rate of oxidation of the combustible gas may be measured in terms of the variation in resistance of the platinum element relative to a reference resistance. The two resistances are generally part of measurement circuit such as a Wheatstone bridge circuit. The output or the voltage developed across the circuit when a combustible gas is present provides a measure of the concentration of the combustible gas. The reference resister generally comprises a compensating, nonactive pelement having chemical and physical characteristics matched as closely as possible with the pelement carrying the catalyst.

Typically, the active pelement and the compensating pelement are deployed within an explosion-proof housing and are separated from the surrounding environment by a porous metal frit. The porous metal frit allows ambient gases to pass into the housing but prevents the "flashback" of flames into the surrounding environment. Such catalytic gas sensors are usually mounted in instruments which, in some cases, must be portable and, therefore, carry their own power supply. It is, therefore, desirable to minimize the power consumption of a catalytic gas sensor.

In recent years, substantial research effort has been devoted to the development of combustible gas detectors using semiconductor technology and silicon micromachining. Although the typical electrical power dissipation of conventional catalytic gas sensors is on the order of 250 to 700 mW, miniature, integrated catalytic gas sensors having electrical power consumption on the order of 100 mW and less are under development. See Krebs, P. and Grisel, A., "A Low Power Integrated Catalytic Gas Sensor," *Sensors and Actuators B*, 13–14, 155–158 (1993).

Figure 1:
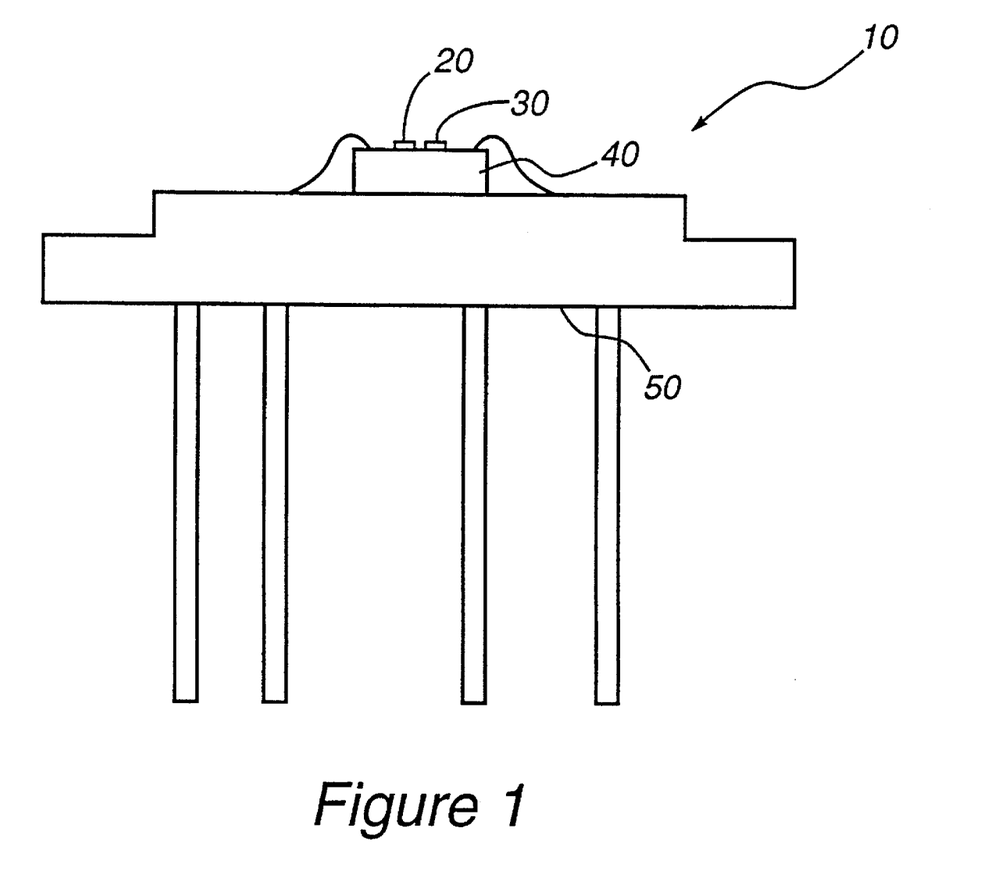
FIG. 1 illustrates a design of a microminiature combustible gas detector.

In general, the overall electronic control circuit design of these microsensors is very similar to that of conventional combustible gas sensors. Referring to FIG. 1, microsensor 10 is provided with both a catalytically active element 20 or detector and a catalytically inactive compensating element 30 or compensator, each of which is used in a measurement circuit such as a Wheatstone bridge circuit. Detector 20 and compensator 30 are disposed upon a microheater chip 40, which is disposed upon a substrate 50.

While the feasibility and advantages of microfabricated sensors have been demonstrated, microfabrication of practical combustible gas microsensors has yet to be achieved. See Wu, Q. et al., "Development of Chemical Sensors Using Microfabrication and Micromachining Techniques," *Sensors and Actuators B*, 13–14, 1–6 (1993). For example, a significant problem to be solved in the commercialization of microminiature combustible gas sensors is the deposition or application of a suitable catalyst upon the microheater chip to form the detector.

Material application techniques in the semiconductor arts are typically categorized as "thick film" techniques or "thin film" techniques. Thick film techniques generally involve material application via a stencil or silk screen technique. The desired material, in a carrier agent or agents, is printed on the target as determined by a pattern of openings cut into the stencil. Carrier agents are removed by drying and the material is occasionally fused on the surface by a baking process. The thick film paste is blended to allow relatively easy processing. The resulting thickness of the applied material depends upon the thickness of the screen or stencil and the percent of solids in the paste. As a result, the thickness of the applied material can range from a thousandth of an inch or less up to 0.125 in. and even greater.

Existing techniques for application of thick films cannot be used to deposit a catalyst film having appropriate dimensions for optimal performance of combustible gas microsensors. The dimensions of the target are too small to accurately align a stencil or silkscreen. Moreover, the pressure required to squeeze the paste (material and carrier agent) through a stencil can break the delicate membranes upon which microsensors are positioned. Finally, the small size of the target footprint will not allow the paste to adhere easily to the surface when the stencil is lifted.

Thin film techniques generally involve material application via vapor deposition techniques, laser evaporation techniques or photolithographic techniques. No carrier agent, silk screen or stencil are required in such techniques. High purity, dense packing and consistent thickness of a few molecules and greater are achievable. In general, the upper limit of the thickness of the applied material obtainable via thin film techniques is approximately 0.001 in. Patterns are created by a photolithographic or similar sacrificial coating technique. Much greater accuracy and resolution are obtainable with thin film techniques than with thick film techniques.

Although catalyst films are presently applied to combustible gas microsensors via thin film techniques as describe above, it has become apparent that thin film techniques cannot achieve a catalyst film of sufficient thickness for acceptable performance of combustible gas microsensors. There are at least three significant problems with the deposition of the catalyst as a thin film. First, the resultant dense packing and consistent film thickness provide a very limited number of catalyst sites and, therefore, a very low signal from the detector. Second, the limited number of catalyst sites causes the detector to have a short life in the presence of even very small amounts of a catalyst contaminant or poison. See e.g., Krebs, P., supra. Third, the dense packing and adhesion to the thin substrate layer characteristic of thin films introduce very high interfacial stresses as the sensor is heated because of differences in thermal coefficients of expansion between the two materials.

It is, therefore, desirable to develop a method of depositing a catalyst system upon a combustible gas microsensor that does no suffer from the above-discussed drawbacks.

SUMMARY OF THE INVENTION

Accordingly, the present invention provides a method of producing a porous refractory support for a catalyst upon a catalytically active detector to be used in a combustible gas microsensor. Such refractory materials are defined as materials suitable to withstand the temperatures to which the detector is heated. In general, the method comprises the step of contacting with a target area defining the shape of the detector a material capable of forming a porous refractory support which adheres to the target area upon the refractory forming material being heated to at least a known conversion temperature. The target area is surrounded by a thermally insulating material, such as silicon dioxide. The refractory forming material in the vicinity of the target area is then heated to or above the conversion temperature. Excess refractory forming material which does not reach the conversion temperature (and thus does not adhere to the target area and the area surrounding the target area) is easily removable.

The refractory forming material in the target area may be heated to its conversion temperature via an external heating source such as a laser, which is capable of substantially accurate targeting and, thus, creation of a substantially accurate isotherm. Preferably, however, the target area is heated via an internal heating source such as an appropriately shaped heating trace defining the boundaries of the catalytically active detector. The insulating material surrounding the target area is not heated above the conversion temperature. The target area may be at or above the conversion temperature when contacted by the refractory forming material or it may be subsequently heated to a temperature at or above the conversion temperature. The refractory forming material is at a temperature below the conversion temperature before being heated in the target area.

The refractory forming material may comprise, for example, a solution of a metal salt which is converted to a refractory metal oxide upon being heated above a known conversion temperature. Preferably, the metal salt is solubilized in a liquid vehicle or carrier, such as water. Other liquid vehicles or combinations thereof capable of solubilizing the metal salt, including certain alcohols, may also be used. In general, the conversion temperature for such refractory forming materials is the temperature at which the metal salt is converted to a refractory metal oxide. The vehicle is preferably chosen to have a boiling point below the conversion temperature to increase the surface area of the resultant refractory support through convective mass transfer associated with boiling.

The refractory forming material may also comprise a slurry including porous refractory particles such as porous aluminum oxide particles. The slurry preferably includes one or more ionically bonded compounds which dissociate in the slurry to act as antiflocculent agents. In general, small particles will form a stable suspension only in the presence of ions. A measure of this effect is provided by the zeta potential. The ions can be supplied by the presence of a salt that decomposes to a nonionic form upon reaching a certain conversion temperature. Above this conversion temperature, a porous refractory matrix is formed.

Preferably, a metal salt which converts to a metal oxide upon reaching the conversion temperature is used as an antiflocculent agent. Formation of the metal oxide upon heating to the conversion temperature also assists in creation of the refractory matrix.

In addition to the examples of refractory ceramic materials discussed above, refractory metals can also be used as high surface area substrates to support active catalyst under the present invention. Compounds such as $TiCl_4$, $WCl_5$ and $KWCl_6$ can be dissolved in liquids or suspended in finely divided form in ionic solutions. These compounds may be transformed into high surface area metals (for example, Ti and W) when heated to known conversion temperatures in a reducing environment (for example, in hydrogen gas). The resulting metals can either serve as a substrate for the active catalyst or can themselves be the active catalyst. As an example of the latter, $H_2PtCl_6$ can be dissolved and then transformed into high surface area Pt metal if the target area is coated with the solution and then heated in a hydrogen environment. In cases where the target area comprises a microminiature heater trace, it may be desirable to provide a thin electrical insulator over the heater trace (for example, silicon dioxide or aluminum trioxide) to prevent the electrical conductivity of the refractory metal from shunting the resistance of the heater trace.

The present invention also provides a microminiature combustible gas sensor comprising a catalytically active detector, which comprises a porous, refractory catalyst support. The porous catalyst support may be fabricated under the above-described method.

The present invention further provides a microminiature combustible gas sensor comprising a catalytically active detector and a diffusion/flow restrictor. The restrictor limits the amount of combustion fuel reaching the catalytically active detector element, thereby causing the catalytic reaction occurring in the vicinity of the catalytically active detector element to become substantially diffusion limited. By causing the catalytic reaction to be substantially diffusion limited, an equilibrium plateau region is reached at lower power input than would occur absent the diffusion restrictor.

Moreover, this diffusion limitation may extend the effective life of the detector in the presence of a catalyst poison. In that regard, because the catalytic reaction is substantially diffusion limited, not all available catalyst sites are utilized during operation of the detector. Therefore, inactivation of available catalyst sites remains "invisible" to an operator of the microsensor until the number of catalyst sites inactivated is great enough to reduce the number of available catalyst sites below that number required to catalyze the diffusion limited reaction.

Still further, the restrictor substantially eliminates convective heat loss caused by the very large temperature gradients in the area of the detector. By reducing or substantially eliminating convective heat loss, the restrictor reduces the power requirement of the microsensor.

Preferably, the restrictor is designed to reduce delay in response time of the microminiature combustible gas sensor associated with diffusion of combustion fuel to the catalytically active detector. To reduce such delays, the distance between the one or more passages in the restrictor which provide fluid connection between the surrounding environment and the catalytically active detector is preferably minimized.

The present invention also provides a microminiature combustible gas sensor comprising a catalytically active detector and a flashback arrestor. The flashback arrestor comprises at least one generally linear capillary providing fluid connection between the catalytically active detector and the environment to be tested. The capillary is dimensioned to prevent flames arising from combustion of combustible gas occurring in the vicinity of the catalytically active detector from passing through the capillary and into the surrounding environment, thereby preventing explosion in the environment.

DETAILED DESCRIPTION OF THE INVENTION

A. Catalyst Deposition

The present method for the application of catalyst to a combustible gas microsensor results in a unique catalyst structure and is generally applicable in any product and/or process employing catalytic burning of a combustible gas. Under the present method, a material capable of forming a refractory, porous matrix upon being heated to or above a known conversion temperature is preferably contacted with a target area and heated to or above the conversion temperature in the vicinity of the target area to form a porous refractory "dot" or "bead" thereon.

The shape of the dot is determined by the isotherm surrounding the (that is, in the vicinity of) the heated target area. This isotherm defines the boundaries of the volume of the refractory material which is heated to or above the conversion temperature. The target area is surrounded by a thermally insulating material which assists in producing an isotherm of a desired size and shape.

Before being heated to the conversion temperature, the refractory forming material is easily removable by, for example, rinsing. After the material in the vicinity of the target area is heated to the conversion temperature, however, that material forms a refractory, porous matrix which adheres relatively strongly to the target area and is not easily removed. Excess refractory forming material outside of the isotherm surrounding the heated target area is not converted and is easily removable. Preferably, such excess refractory forming material is removed by rinsing with a solvent for a salt therein to take advantage of both solubilization and mechanical force to remove the excess refractory forming material. The present method thus enables substantial control over the deposition of a porous catalyst support structure upon a target area defined by a heater trace formed upon a microheater chip.

In general, the refractory forming material is present in a liquid vehicle or carrier when applied to the target area. In one embodiment, the refractory forming material comprises a solubilized metal salt (solubilized in a liquid vehicle such as, for example, water) which forms an insoluble metal oxide upon heating above a known conversion temperature. Examples of such metal salts include aluminum nitrate and magnesium nitrate, which are converted to water-insoluble, refractory aluminum oxide and magnesium oxide, respectively, upon heating.

The refractory forming material may also comprise refractory, porous particles which become incorporated into the porous refractory matrix upon heating the refractory forming material above the conversion temperature. Preferably, such particles are chosen to have a high surface area per unit weight. The refractory forming material may comprise, for example, a slurry of suspended, refractory particles, such as aluminum oxide particles. In one embodiment, alpha and/or gamma aluminum oxide suspended in $H_2O$, aluminum nitrate and isopropyl alcohol were used. Aluminum oxide suspended in $H_2O$, aluminum nitrate and cerium nitrate has also been used.

The constituents of the present solutions and slurries comprising the refractory forming material can vary widely in concentration. For example, if water is chosen as the carrier the metal salt (for example, aluminum nitrate) which forms a metal oxide upon reaching a known conversion temperature is preferably present in the range of approximately 5 to 50% by volume.

If high surface area particles such as aluminum oxide particle are present to form a slurry, such particles are preferably present in the range of approximately 0 to 50% by weight. In case in which a salt of a metallic oxidation catalyst is present in the refractory forming material, the salt of the metallic oxidation catalyst is preferably present in the range of approximately 0 to 20% by volume and most preferably in the range of approximately 5 to 10% by volume. In the case that aluminum nitrate is used in combination with a salt of a metallic oxidation catalyst, cerium nitrate is preferably present in the range of approximately 0 to 10%.

Moreover, a wide range of particle sizes may be used in the refractory forming material of the present invention. In one embodiment, high purity aluminum oxide powder of 0.05 micron particle size and having a surface area of approximately 85 square meters per gram was used. The tremendous surface area of such particles provides many sites for catalytic metals to be exposed to combustible gas.

Other refractory oxides suitable for use in the present invention include silica, titania, magnesia, thoria, zirconia; mixed oxides such as silica-alumina, silica-zirconia, alumina-titania, etc, and ternary oxides; crystalline aluminosilicate zeolite materials such as erionite, mordenite, faujasite and natural clays such as montmorilonite.

The high surface area catalyst support/substrate produced upon heating/conversion of the refractory forming material provides a number of significant advantages over existing combustible gas microsensors. For example, the large number of available catalyst sites provides a greater signal than obtainable with previous designs. Moreover, the large number of available catalyst sites creates a "reserve" of catalyst such that greater contaminant loading is required to inhibit the output of the microsensor than experienced with previous combustible gas microsensors.

As discussed above, an oxidation catalyst may be present in the refractory forming material. For example, Group VIII metals (especially, Pd, Pt, Ir and Rh) may be present in the refractory forming material in the form of a soluble metal salt. Preferably, Pd or Pt are used in the form of a soluble metal salt such as tetra-amine palladium nitrate (TAPN) or chloroplatinic acid ($H_2PtCl_6$ $6H_2O$). Such a catalyst solution may also or alternatively be applied to the refractory dot after formation thereof.

Figure 2A:
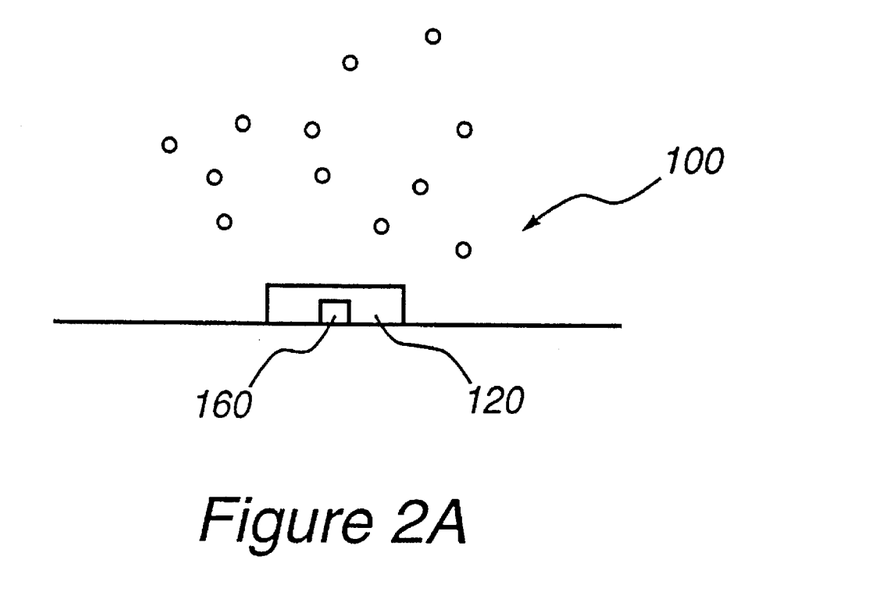
FIGS. 2A and 2B illustrate an embodiment of the present method for application of a catalyst to a heated target.
Figure 2B:
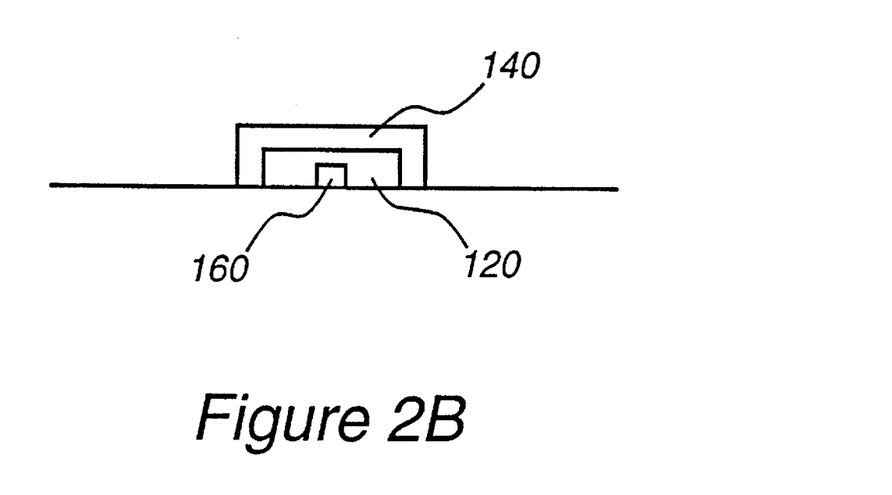

As illustrated in FIGS. 2A and 2B, a refractory forming material 100 such as described above is contacted with a target 120 upon which a ceramic bead 140 is to be formed. Preferably, target 120 is in thermal connection with a heating element 160 for heating target 120. For example, target 120 may comprise a semiconductor wafer including a platinum heating element embedded therein. In general, the present high surface area catalyst substrate can be deposited upon virtually any microsensor comprising a suitable heater trace (defining a target area). An example of a suitable electronic circuit and microheating element for the present catalyst/substrate application method is disclosed in Krebs, P., supra, the disclosure of which is incorporated herein by reference.

Upon supplying sufficient heat to target 120 via microheating element/trace 160, material mixture 100 surrounding heated target 120 is converted to a porous refractory matrix 140 which adheres to target 120. Target 120 may be heated above the fusion temperature prior to the application of material mixture 100 or subsequent thereto.

By way of example, the conversion temperature for aluminum nitrate is 150° C., while the conversion temperature for cerium nitrate is 200° C. One may wish, however, to heat target 120 to a much higher temperature to achieve conversion more quickly and/or to achieve a thicker porous, refractory matrix.

The density/porosity of resultant porous refractory matrix 140 can be controlled via the variation of a number of parameters including, for example, (I) the amount of liquid material evaporated from the material mixture; (ii) the rate of evaporation (via control of power (heat) regulation during the liquid evaporation process); (iii) the extent of drying before heating to conversion temperature; (iv) adjustment of mixture/solution density and (v) adjustment of the amount of hygroscopic crystals.

When the target 120 is heated to an appropriate conversion temperature without previous drying/evaporation of refractory forming material 100, the vigorous boiling of the liquids of refractory forming material 100 results in significant particle motion. When vaporization is complete, the temperature rises quickly and conversion occurs faster than the particles can settle into an optimum packing arrangement, thereby resulting in high porosity. When refractory forming material 100 is allowed to dry before heating to the conversion temperature, crystals of, for example, aluminum nitrate and other agents form on the surface. As compounds such as aluminum nitrate may be hygroscopic, some water may be bound in material mixture 100. When sufficient power is supplied to heat target 120 to or above the conversion temperature, less boiling (and thus less particle motion) occurs than in the case of no drying. Particle packing density is, therefore, higher and porosity is lower.

Application of the refractory forming material as a spray to a target heated to or above the conversion temperature may provide a method of optimizing the active surface area of the catalyst substrate/support to facilitate maximum catalytic activity per unit volume of catalytic material.

Upon impact with the heated target, the temperature of the sprayed material rapidly rises. Any liquids are evaporated upon contact. The resulting solids are formed into a porous, refractory structure. Porosity achieved by this process may be higher than achievable by a coating application of a liquid, slurry, or solid upon a target and then heating the target to the conversion temperature.

It is believed that the creation of individual spray droplets allows rapid temperature rise of each droplet upon impact. The porous refractory matrix is formed as each droplet hits. Particles do not settle into optimum packing density as would occur if applied cold. Variation in the properties of the resultant film (for example, the size/thickness thereof and the porosity thereof) are obtainable via adjustment of numerous parameters including drop size, target temperature, transit duration from drop formation to impact, transit temperature from drop formation to impact, and initial droplet temperature.

After contact with target 120 and heating to or above the conversion temperature, simply rinsing the sample with a liquid such as water removes all excess refractory forming material 100. After drying the rinsed sample, only refractory matrix or dot 140 sized according to the isotherm of conversion around target 120 remains. The shape of dot 140 is dependent upon the target/heater configuration. As appreciated by one skilled in the art, the thickness of dot 140 is dependent upon a number of variables, including the amount of refractory forming material 100 applied before heating and the temperature to which target 120 is heated. The process step of contacting refractory forming material 100 with heated target 120 can be repeated one or more times to increase the size of dot 140.

The present method is thus particularly useful for applying a relatively thick film catalyst material upon a semiconductor wafer. The placement accuracy of such catalyst material under the present invention substantially exceeds that possible under existing techniques. Moreover, the costs associated with the application of the catalyst are significantly less that the costs associated with existing techniques.

EXAMPLE

In one embodiment of the present method, a bead or dot as described above is formed upon both the catalytically active detector and the catalytically inactive compensator of a microsensor. In one experiment, distinct material slurries were used in forming the detector and the compensator. The catalyst slurry (that is, the slurry used in forming the detector) comprised water, aluminum nitrate, suspended aluminum oxide particles, cerium nitrate and approximately 6% TAPN. The composition of the compensator slurry was similar, but did not include TAPN and was further modified by the addition of a 2% solution of hydrogen tetrachloroaurate in $H_2O$ (2.0 grams of hydrogen tetrachloroaurate in 50 mL of $H_2O$).

The compensator was formed first. Initially, the compensator slurry was poured on the chip. Excess slurry was removed so that only a film held by surface tension remained. The film was dried with hot air. The film may also be dried with room temperature air, but the drying process is slower. Power was then applied to the heating element at approximately 23 mA for 20 seconds. A visual change was observed as the aluminum nitrate in the compensator slurry converted to aluminum oxide and the aluminum oxide particles of the compensator slurry were formed into an insoluble refractory matrix.

The chip was cooled below the conversion temperature before another application of compensator slurry by application of a power shunt. After application of the power shunt, the current dropped approximately 15.0 mA. The material application process described above was repeated once. When finished, the chip was cooled and rinsed with water to remove all refractory forming material not converted into an adherent porous refractory matrix in the area defined by the conversion isotherm.

After formation of the compensator, the detector was formed. In formation of the detector, the catalyst slurry was poured on the chip. Excess catalyst slurry was removed as described above. The remaining catalyst slurry was then dried. The detector element was heated by application of approximately 21 mA to fuse the catalyst slurry into a ceramic matrix. The detector element was then cooled and excess water-soluble catalyst slurry was removed by a water rinse. This process was repeated four times. After the fourth and final application of catalyst slurry and conversion thereof, a catalyst solution comprising TAPN and water was applied to the chip. Excess solution was removed to leave only an amount held by surface tension. The chip was dried and a current of approximately 21 mA was applied to the detector for approximately ten (10) seconds.

The microsensor was washed in water to remove all water soluble chemicals. Warm water (having a temperature of approximately 110 F) appeared to provide the best results. After drying, the microsensor was "activated" by ramping the power supply to approximately 26 mA in ambient air, preferably for a minimum of 24 hours. After such an activation period, the voltage drop (span) measured at a constant current was found to settle to a substantially constant output.

In addition to the example described above, the compensator may also be formed using a slurry as described for the detector, except the compensator element is rendered inactive by exposure to a heavy metal such as gold or chrome or exposure to a catalyst poison such as hexamethyldisiloxane. Several deactivation methods suitable for fabrication of a compensator for use in the present invention are set forth in U.S. patent application Ser. No. 07/873,387, the disclosure of which is incorporated herein by reference.

The present thick film detectors and compensators catalysts exhibited zero misalignment with the chip heater trace (isotherm). Moreover, as there was substantially no tolerance stackup in alignment, multiple process applications were successfully performed in building a thicker matrix/dot as desired. Preferably, a dot thickness of between approximately 0.0005 and 0.015 in. is obtained. More preferably, a dot thickness of between approximately 0.002 and 0.006 in. is obtained.

EXPERIMENTAL RESULTS

Figure 3A:
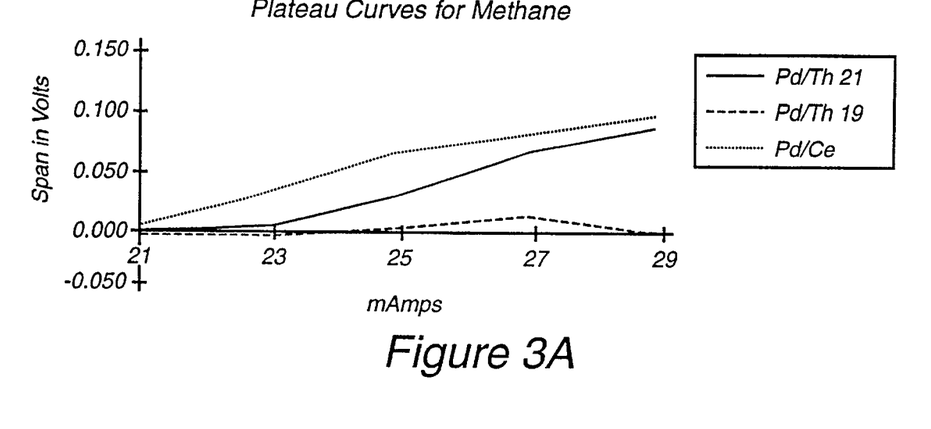
FIGS. 3A through 3C illustrate the performance of a microminiature combustible gas detector comprising a catalyst applied using the method illustrated in FIGS. 2A and 2B.
Figure 3B:
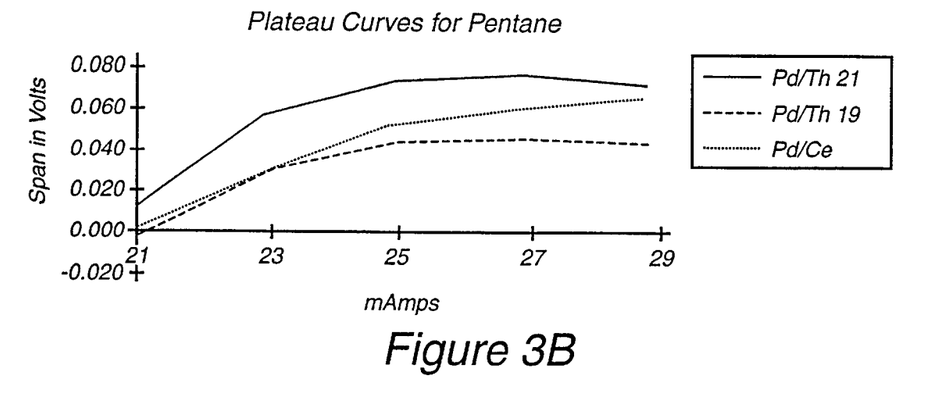
Figure 3C:
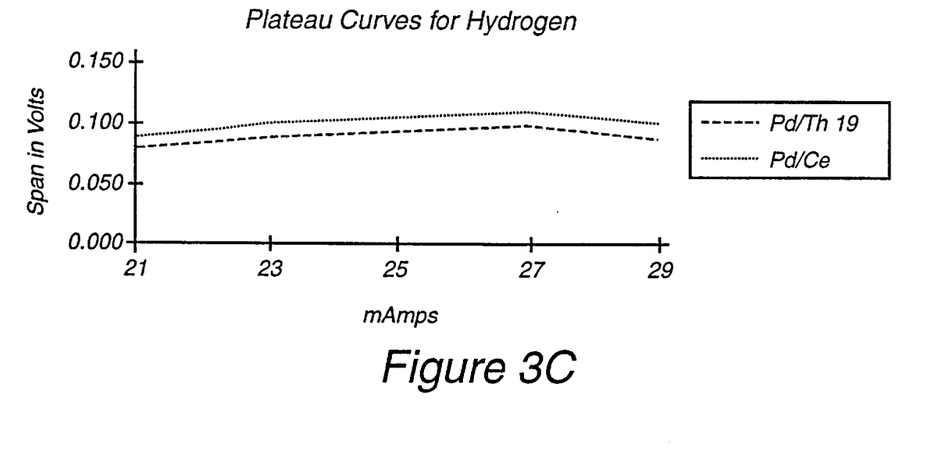

FIGS. 3A through 3C illustrate a series of experiments demonstrating the performance attainable with microsensors fabricated under the present method using several metal catalysts. In FIGS. 3A and 3C, the designation Pd/Th 21 and Pd/Th 19 refer to two experiments with detectors comprising a palladium/thorium catalyst mixture, while the designation Pd/Ce refers to an experiment with a detector comprising a palladium/cerium catalyst mixture. As illustrated, such microsensors exhibit a desirable plateau curve and provide a much greater output signal than existing microsensors in which the catalyst was deposited as a thin film.

Figure 3D:
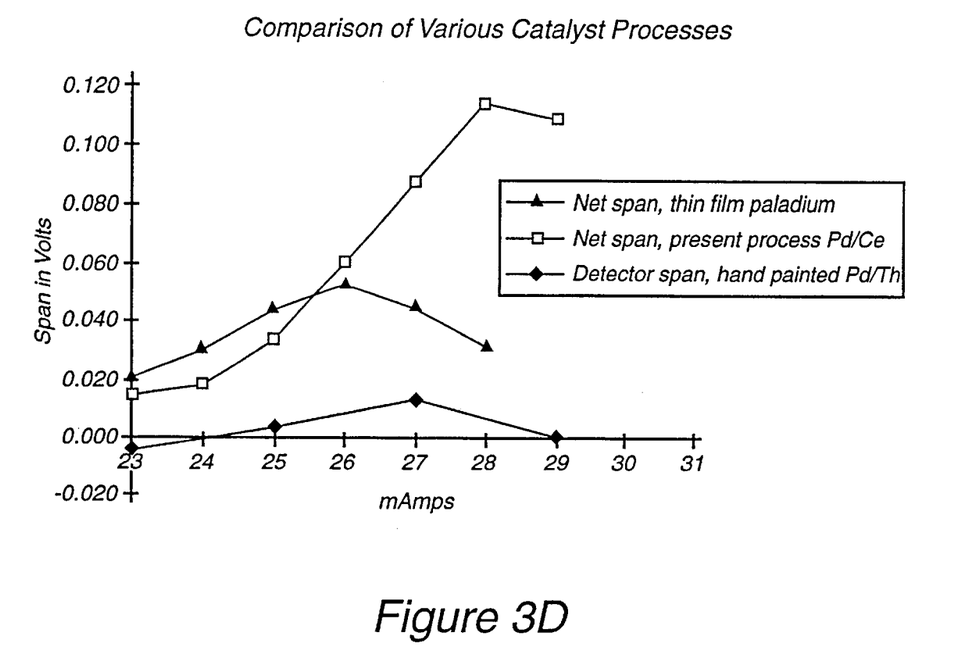
FIG. 3D illustrates the greater signal output provided by the present invention as compared to existing combustible gas microsensor designs.

FIG. 3D illustrates the improvement in signal output achieved using a microsensor fabricated under the present invention as compared to (i) a microsensor in which the detector was fabricated by a thin-film deposition technique and (ii) a microsensor in which the detector was fabricated by a hand-painting technique.

B. Restriction of the Amount of Gas Reaching the Microsensor.

Figure 4A:
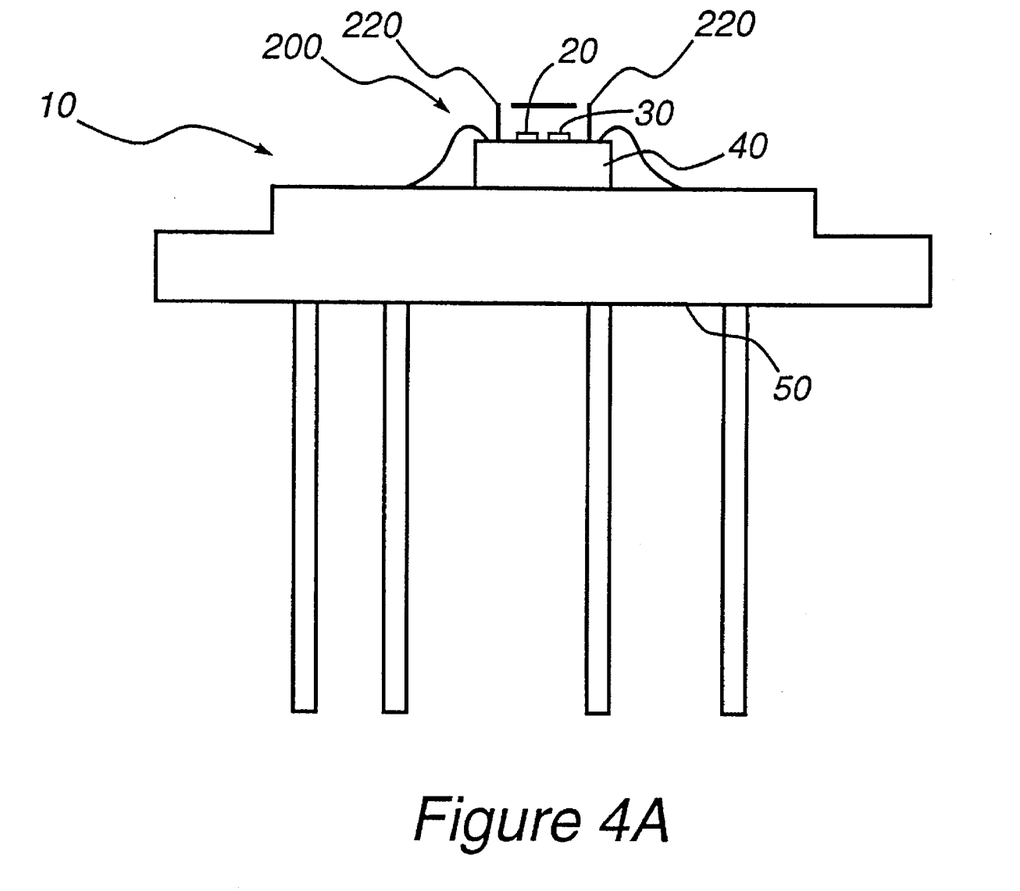
FIGS. 4A through 4F illustrate a number of embodiments of a diffusion/flow restrictor structure for use in a microminiature combustible gas detector.
Figure 4B:
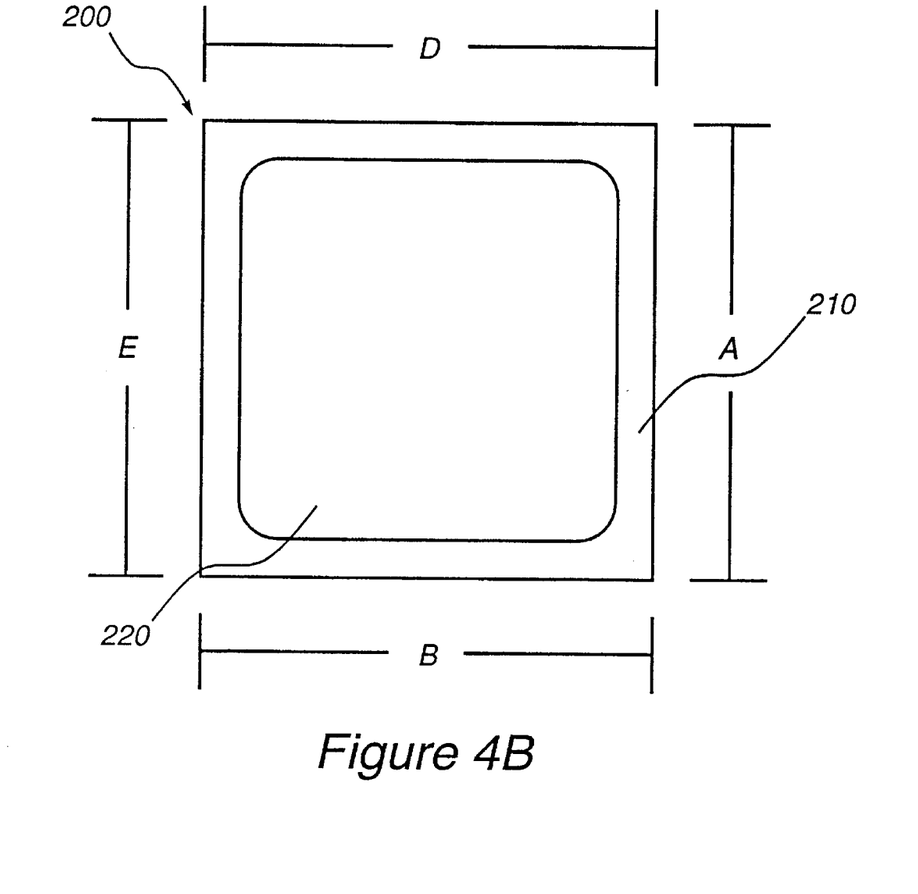
Figure 4C:
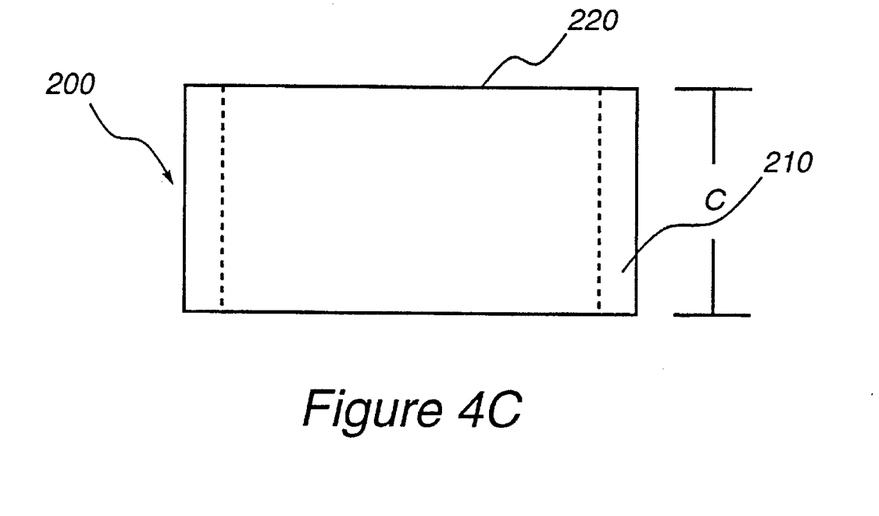
Figure 5:
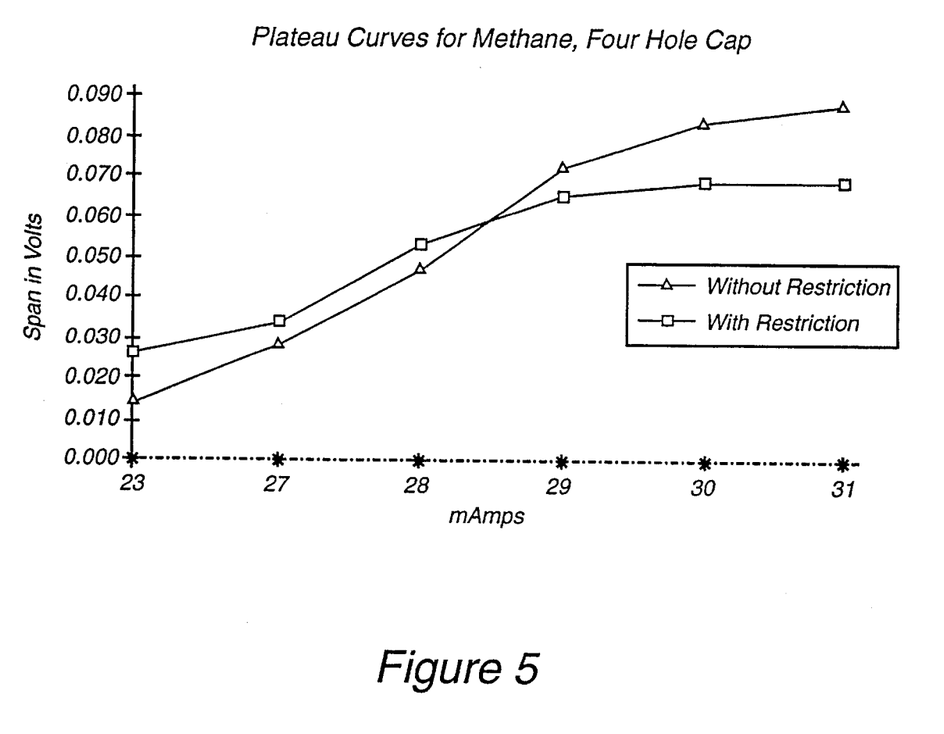
FIG. 5 illustrates the use of a diffusion/flow restrictor structure to achieve a plateau region at lower currents.

The present invention also provides a miniature diffusion/flow restriction structure for limiting the amount of gas reaching the catalytically active detector element of a microminiature combustible gas sensor and for reducing heat loss arising from convective heat transfer. Referring to FIG. 4A, it has been discovered that a restriction structure 200 comprising at least one passage 220 therein provided over the hot catalyst surface of a microminiature heater 10 results in achievement of a plateau region at lower temperature/current. This effect is illustrated for one experiment in FIG. 5.

It is generally found that upon increasing the temperature of a catalyst element above the temperature at which substantial catalytic combustion occurs that a plateau region is eventually reached in which the catalytic reaction reaches an equilibrium given the available oxygen, combustible gas and catalytic sites. In this plateau region, supply of additional power does not significantly affect the reaction rate or the heat liberated in the reaction. In the plateau region, the output across the measurement circuit thus remains substantially constant as the current/temperature is increased. In general, it is desirable to operate the combustible gas detector within the plateau region.

It is believed that by restricting the amount of combustible gas which may reach the catalyst surface of the detector element, the catalytic reaction becomes substantially diffusion limited. By restricting the availability of combustible gas and oxygen, the equilibrium state (plateau region) for the combustion reaction is reached at a lower power level. By achieving a plateau region at a lower temperature/current via the use of restriction structure 200 to achieve diffusion limitation, microminiature combustible gas detector 10 may be operated at a lower temperature/current, thereby reducing power requirements. Moreover, as set forth above, diffusion limitation may extend the effective life of the detector in the presence of a catalyst poison.

Diffusion limitation may, however, detrimentally impact the overall microsensor performance by decreasing response time. Responses to rapid changes in the combustible gas concentration in an environment may be slowed because of the time delay associated with diffusion through restrictor or limiter 200. However, because the distance between passage(s) 220 and the detector and compensator elements is maintained relatively short or, preferably, minimized, diffusion delays are reduced, and the response time of the microsensor is not adversely affected.

The construction and design of a number of embodiments of restrictor 200 is illustrated in FIGS. 4B through 4H. The dimensions of one embodiment of a restriction structure 200 are described in FIGS. 4B and 4C. In this embodiment, the length A of a body member 210 of restriction structure 200 is approximately 0.062 in. The width B is approximately 0.050 in. and the height C is approximately 0.040 in. Passage 220 has a width D of approximately 0.037 in. and a length E of approximately 0.050 in. The radius of curvature of the corners of passage 220 is approximately 0.016 in.

Body member 210 is preferably constructed of an insulating material such as a ceramic to reduce conductive heat loss. In one embodiment, body member 210 was constructed by drilling two overlapping holes through an appropriately sized block of ceramic material (for example, sized as set forth in FIGS. 4B and 4C) via ceramic machining techniques as known in the art. The perimeter of the overlapping holes was then machined to provide the shape of passage 220.

Figure 4D:
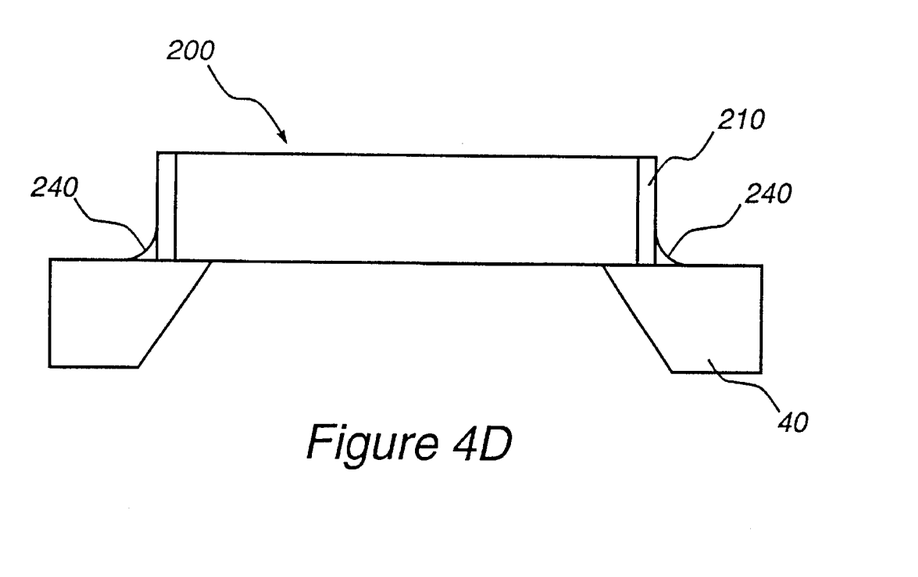
Figure 4E:
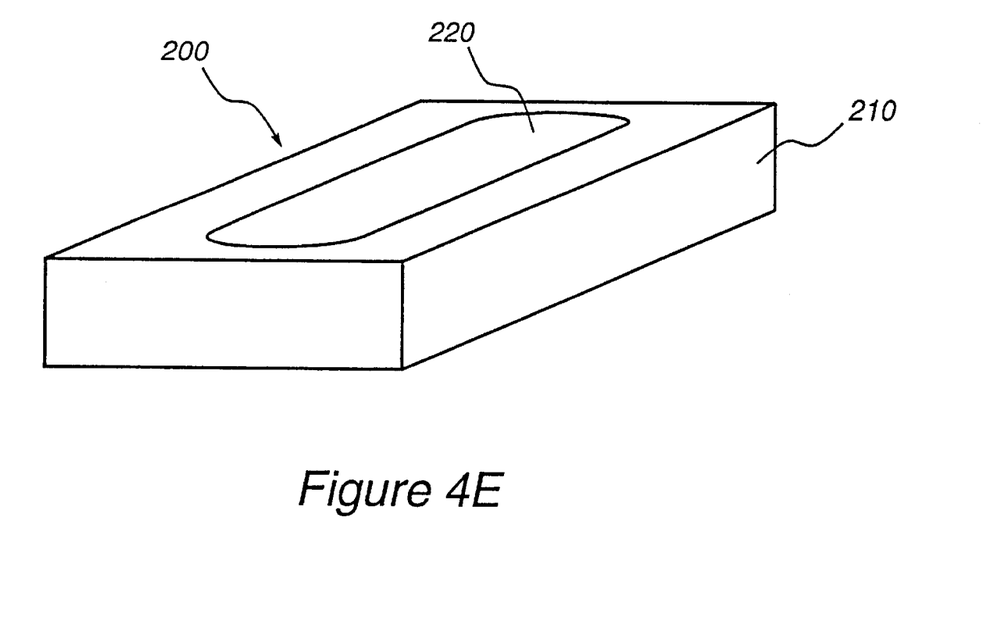

The attachment of body member 210 to microheater chip 40 is best illustrated in FIG. 4D. In this embodiment, body member 210 was attached to microheater chip 40 using an adhesive 240 such as an epoxy. In general, any type of two-part epoxy is suitable for use in the present invention. In one experiment, EPOXI-PATCH®, available from Dexter of Pittsburg, Calif. was used as adhesive 240. Adhesive 240 may be applied, for example, by placing a small amount of adhesive 240 on the end of a wire and contacting adhesive 240 with body member 210 where body member 210 contacts microheater chip 40. Because of the small dimensions of body member 210 and microheater chip 40, this technique was performed with the aid of a microscope.

Figure 4F:
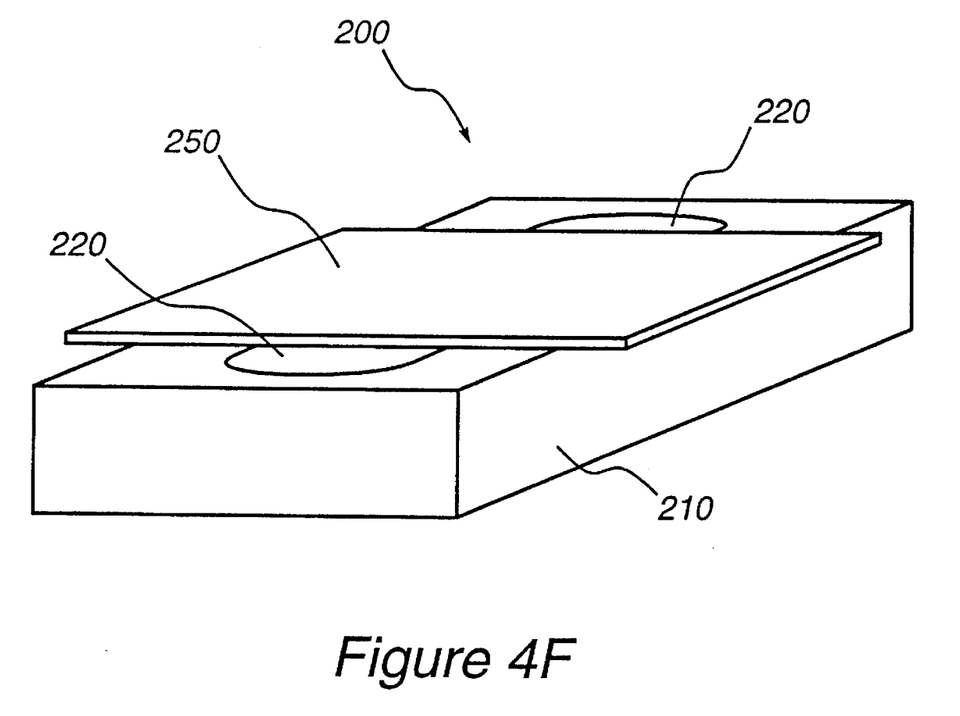

The area of the opening of passage 220 may be reduced by providing a cover member 250 as illustrated in FIG. 4F. Like body member 210, cover member 250 is preferably fabricated from an insulating material to reduce conductive heat loss. As shown in FIG. 4F, cover member 250 is attached (via, for example, epoxy) to body member 210 to create two passages 220. Cover member 250 may be attached to body member 210 using adhesive 240 using a technique as discussed above. In some cases, adhesive 240 may contact detector 20 and/or compensator 30. Such adhesive 240 may inactivate detector 20 and should be removed, for example, by elevating the temperature of detector 20 and/or compensator 30 to a temperature suitable to "burn off" the adhesive.

Although passages 220 are shown to be on the top of restrictor 200 in FIGS. 4A through 4H, passages 220 may be positioned anywhere therethrough. For example, in one experiment passages 220 were positioned on the bottom of restrictor 200 by machining raised portions in the bottom perimeter of restrictor 200 such that when restrictor 200 was attached to microheater chip 40, combustion fuel could diffuse/flow through the raised portions.

Preferably, the area/size of one or more passages 220 in body member 210 are minimized to increase the corresponding diffusion limitation of the oxidation reaction. As the amount of combustion fuel reaching detector 20 is reduced, however, the output signal provided by detector 20 is also reduced. The cross-sectional area of passage(s) 220 must be sufficiently large to enable enough combustion fuel to diffuse to detector 20 to provide a signal to noise ratio adequate to distinguish between changes in combustible gas concentration.

Figure 4G:
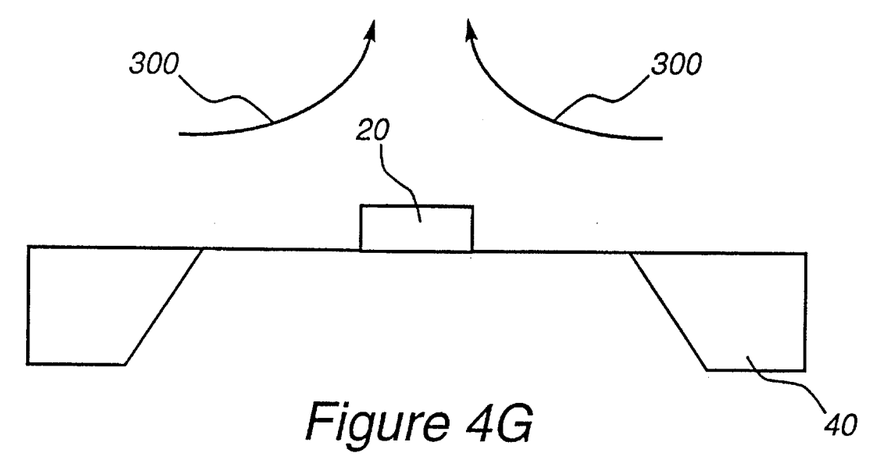
FIG. 4G illustrates convective heat transfer occurring without the use of a restrictor.
Figure 4H:
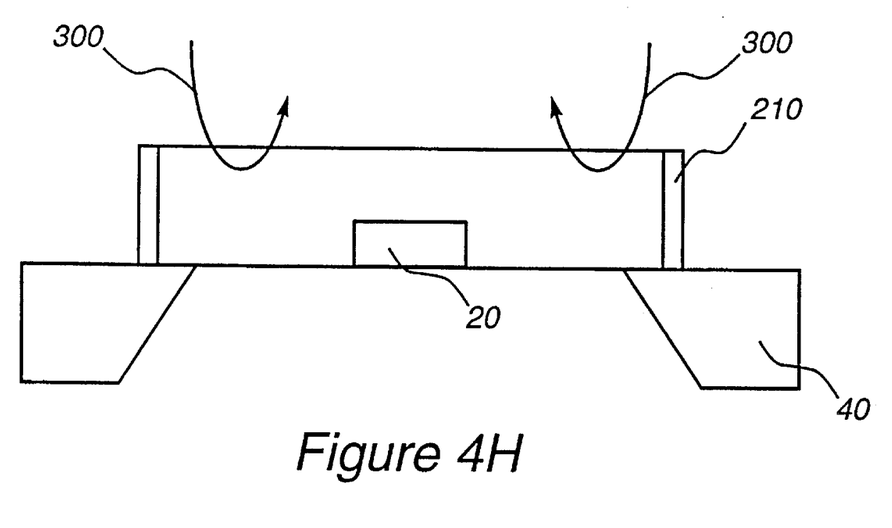
FIG. 4H illustrates the reduction of convective heat transfer using a restrictor

Restriction structure 200 provides an additional benefit by reducing heat loss in the high temperature area surrounding the detector and compensator arising from convective heat transfer. This reduction in heat loss results in a reduction in power requirements to achieve combustion temperatures. FIG. 4G provides an idealized representation of convective heat transfer currents (represented by arrows 300) that arise because of the large temperature gradient in the area of detector 20. FIG. 4G illustrates the change in such convective heat currents 300 upon provision of restrictor 200 as described in FIGS. 4B through 4E. The viscous drag created by the internal walls of body member 210 reduce the overall convective heat loss. Convective heat loss may be further reduced by provision of cover member 250 as illustrated in FIG. 4F. Morover, a number of experiments showed that positioning of passages 220 on the bottom of restrictor 200 may be optimal for reduction of heat loss.

C. Prevention of Flashback

As set forth above, a porous metal frit is generally used to prevent flashback in conventional combustible gas detectors. Such frits must be made of small individual metal particles but have a porosity adequate to allow gas to diffuse or flow therethrough unimpeded, and still act to extinguish any flames resulting from the combustion of gas within the detector. Similar porous metal frits have been proposed for use with microminiature combustible gas detectors. The manufacture of such porous metal frits, however, is quite difficult because it is very difficult to achieve a desirable porosity while maintaining the frit sufficiently dense to prevent explosion outside the sensor.

Figure 6:
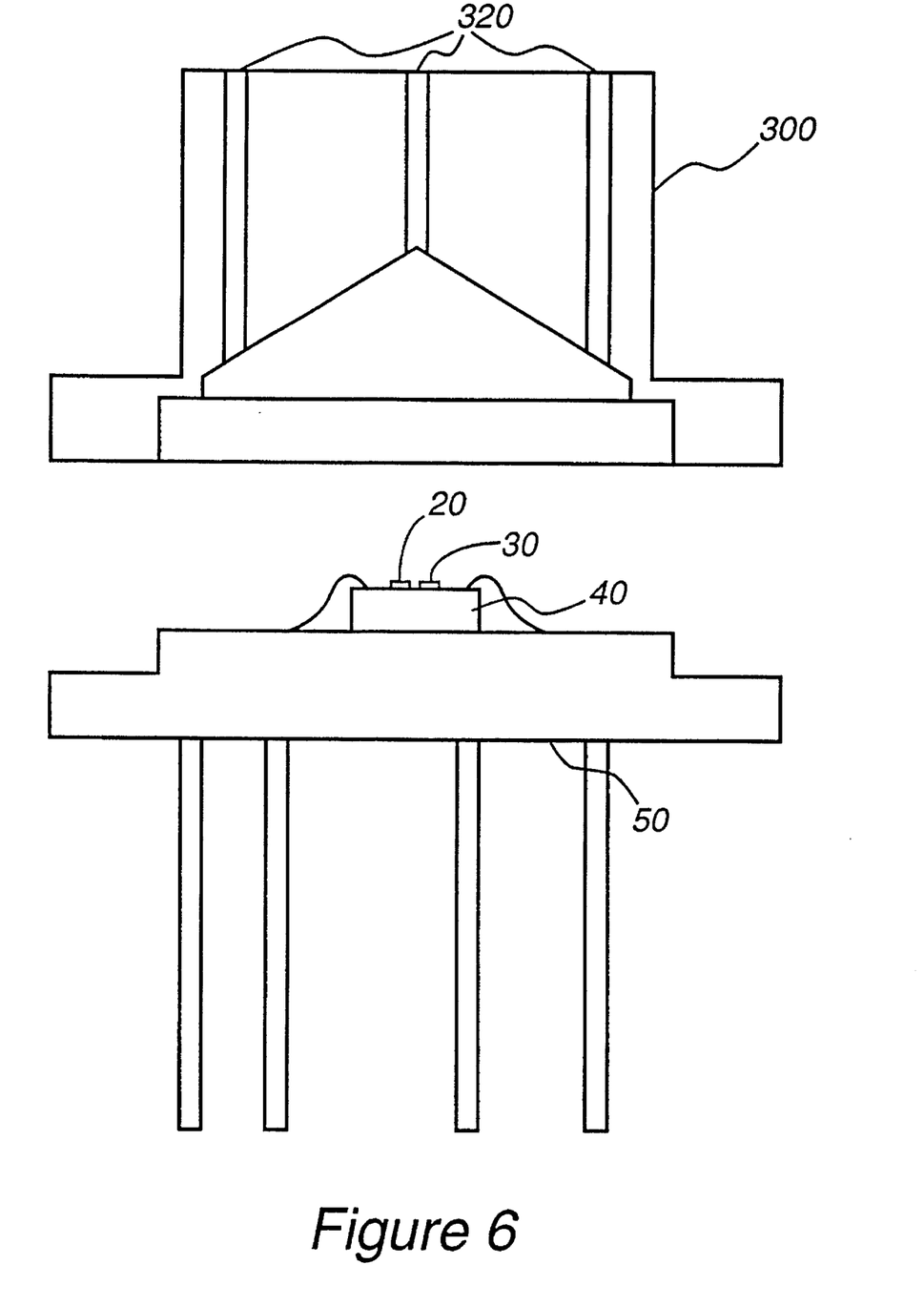
FIG. 6 illustrates a flashback arrestor for use in connection with microminiature combustible gas detectors.

It has been discovered that the relatively small catalytic dot or bead used in the present microminiature combustible gas sensors (as compared to conventional pellistors) results in a proportionally small fuel consumption requirement, and, therefore, a linear path, capillary-type flashback arrestor 300 will allow sufficient unimpeded fuel flow and may be used in connection with such microsensors. Flashback arrestor 300 comprises one or more flashback arrestor capillaries 320 as illustrated in FIG. 6.

The design and performance of flashback arrestors comprising substantially linear capillaries is discussed in *Miners' Lamps Committee, Memorandum No. 4*, "Record of Research on the Passage of Flame through Perforated Plates and through Tubes of Small Diameter," published by Mines Department, London, United Kingdom (1921) and Williams, F. A., *Combustion Theory: The Fundamental Theory of Chemically Reacting Flow Systems,* Addison-Wesley Publishing Company, Inc., Palo Alto, Calif., pp. 187–201 (1965), the disclosures of which are incorporated herein by reference.

Although the required length and diameter of capillaries 320 is preferably determined experimentally for a given microsensor design, Williams, supra, provides a mathematical model which may be used in determine an appropriate length and diameter. Because of the relatively small power requirements of combustible gas microsensors and the correspondingly small flame pressure and flame velocities of such microsensors, however, a length to diameter ratio less than predicted by the model of Williams may be suitable for the present invention. For example, in one experiment with a combustible gas microsensor comprising a supported catalyst as described above, capillaries having a diameter of 0.031 in. and a length of 0.25 in. were found adequate.

Preferably, several capillaries 320 are used to ensure that capillaries 320 do not create a diffusion limitation. Although diffusion limitation may be beneficial as described above, the length through which combustion fuel must travel upon entering capillaries 320 until reaching detector 40 and compensator 30, can create undesirable delays in response time.

Because the required diameter of flashback arrestor capillaries 320 and the length the flashback arrestor capillaries 320 are easily established (whether by experiment or mathematical model) and thus known (unlike the case of porous metal frits), flashback arrestor 300 is easily manufactured. Moreover, quality control is easily maintained.

Although, the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of producing a porous refractory support for a catalyst for a catalytically active detector to be used in a microminiature combustible gas sensor, the method comprising the steps of:

a. surrounding a target area with a thermally insulating material to define the shape of the detector;

b. bringing into contact with the target area a material capable of forming the porous refractory support upon the refractory forming material reaching a temperature of at least a known conversion temperature;

c. heating the refractory forming material in the target area to at least the conversion temperature, the refractory forming material being at a temperature below the conversion temperature before coming into contact with the target area, the thermally insulating area surrounding the target area remaining below the conversion temperature, thereby forming the porous refractory support in the shape of the target area; and d. removing excess refractory material which has not been heated to the conversion temperature.

2. The method of claim 1 wherein the target area is heated above the conversion temperature before the refractory forming material is contacted therewith.

3. The method of claim 1 wherein the target area is heated above the conversion temperature after the refractory forming material is contacted therewith.

4. The method of claim 1 wherein the refractory forming material comprises a salt of a metal catalyst.

5. The method of claim 1 further comprising the step of applying a metal catalyst to the porous refractory support.

6. The method of claim 1 wherein the refractory forming material comprises a slurry including refractory porous particles.

7. The method of claim 6 wherein the refractory porous particles are aluminum oxide particles.

8. The method of claim 1 wherein the refractory forming material comprises a metal salt which is converted to a refractory metal oxide upon being heated to the conversion temperature, the refractory forming material further comprising a liquid vehicle in which the metal salt is soluble.

9. The method of claim 8 wherein the metal salt is aluminum nitrate.

10. The method of claim 8 wherein the refractory forming material further comprises refractory porous particles.

\* \* \* \* \*